US00PP28499P3

(12) United States Plant Patent
Kordes

(10) Patent No.: US PP28,499 P3
(45) Date of Patent: Oct. 10, 2017

(54) MINIATURE ROSE PLANT NAMED 'KORPOT068'

(50) Latin Name: *Rosa hybrida*
Varietal Denomination: KORpot068

(71) Applicant: W. Kordes Söhne Rosenschulen GmbH & Co. KG, Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Offenseth-Sparrieshoop (DE)

( * ) Notice: Subject to any disclaimer, the term of this patent is extended or adjusted under 35 U.S.C. 154(b) by 29 days.

(21) Appl. No.: 14/998,608

(22) Filed: Jan. 20, 2016

(65) Prior Publication Data

US 2017/0208714 P1 Jul. 20, 2017

(51) Int. Cl.
*A01H 5/02* (2006.01)

(52) U.S. Cl.
USPC ..... Plt./117

(58) Field of Classification Search
USPC ..... Plt./117
See application file for complete search history.

*Primary Examiner* — Keith Robinson
(74) *Attorney, Agent, or Firm* — Samuel R. McCoy, Jr.

(57) ABSTRACT

'KORpot068' is a new and distinct variety of *Rosa hybrida* which is characterized by the combination of a compact and upright growth habit, moderately vigorous growth, an abundance of large double-type flowers, cream white flower color, and good disease resistance. The new variety propagates successfully by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORpot068'.

BACKGROUND OF THE INVENTION

The present invention relates to a new and distinct *Rosa hybrida*, miniature rose cultivar, which has been given the variety denomination of 'KORpot068'. Its market class is PLT/116.

Parentage: The *Rosa hybrida* cultivar 'KORpot068' originated as a naturally occurring mutation of *Rosa hybrida* 'KORpot042' (U.S. patent application Ser. No. 14/544,576). 'KORpot068' was discovered in August of 2013 at the inventor's nursery in Offenseth-Sparrieshoop, Germany. 'KORpot068' was discovered by Tim-Hermann Kordes as a branch mutation and was selected for its cream white flowers.

Asexual Reproduction: The first asexual propagation of 'KORpot068', by way of stem cuttings, was performed in August of 2013 at the inventor's nursery in Offenseth-Sparrieshoop, Germany. Subsequently, 'KORpot068' has been successfully propagated by stem cuttings in Jackson County, Oreg. These initial and other subsequent propagations conducted in controlled environments demonstrate that 'KORpot068' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot068'. These traits, in combination, distinguish 'KORpot068' as a new and distinct cultivar.

1. *Rosa hybrida* 'KORpot068' exhibits a compact and upright growth habit; and
2. *Rosa hybrida* 'KORpot068' exhibits moderately vigorous growth; and
3. *Rosa hybrida* 'KORpot068' exhibits good disease resistance; and
4. *Rosa hybrida* 'KORpot068' exhibits an abundance of flowers; and
5. *Rosa hybrida* 'KORpot068' exhibits a double petal count; and
6. *Rosa hybrida* 'KORpot068' exhibits a large flower size for a miniature rose; and
7. *Rosa hybrida* 'KORpot068' exhibits a cream white flower color, at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot068', taken from six month old plants.

DETAILED BOTANICAL DESCRIPTION

The following is a detailed botanical description of a new and distinct variety of *Rosa hybrida* known as 'KORpot068', based upon field observations made in October of 2015, from six month old container-grown plants in a greenhouse environment in Jackson County, Oreg. Those skilled in the art will appreciate that certain characteristics will vary with older or, conversely, with younger plants. 'KORpot068' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORpot068' and comparisons with other varieties of *Rosa hybrida* are provided below.

General plant description:

*Growth rate*.—Moderately vigorous.

*Growth habit*.—Compact and upright.

*Mature dimensions*.—18 to 20 cm tall and 18 cm wide, on average, when grown as a 15 cm nursery pot.

*Cold hardiness*.—Unknown.

*Propagation*.—Stem cuttings.

*Disease resistance*.—Good resistance to powdery mildew (*Sphaerotheca pannosa*), blackspot (*Diplocarpon rosae*) and rust (*Phragmidium* sp.) diseases in a greenhouse environment in Jackson County, Oreg.

Root system: Fibrous.

Stems:

*Stem color*.—Young stems are Yellow-Green Group 146A; mature stems are Yellow-Green Group 146A.

*Anthocyanin intonations*.—Greyed-Red Group 181A intonations are present on new growth.

*Stem surface texture*.—Both immature and mature stems exhibit a smooth texture.

*Stem dimensions*.—Typical mature stems are approximately 15 cm long and 6 mm in diameter.

*Prickles*.—Incidence — Present; 20 prickles per 10 cm of stem, on average. Size — Average length is 5 mm. Immature prickle color — Greyed-Red Group 182A. Mature prickle color — Greyed-Red Group 182B and senescing to Greyed-Orange 163D. Anthocyanin intonations — Greyed-Purple Group 184B is present on immature prickles. Shape — Deeply concave. Texture — Smooth.

Leaves:

*Arrangement*.—Imparipinnate compound leaves; mature axillary leaves consisting of 5 leaflets.

*Attachment*.—Petiolate.

*Dimensions*.—130 mm long and 90 mm wide, on average.

*Abundance*.—Very abundant; normally 25 to 40 leaves.

*Stipules*.—Size — 15 mm long and 5 mm wide. Stipule color — Yellow-Green Group 146B. Anthocyanin intonations — None. Stipitate glands — Limited; few glands present at margins and abaxial surface. Margins — Finely serrated stipitate glands. Texture, adaxial surfaces — Glabrous. Texture, abaxial surfaces — Rugose. Apex — Apiculate. Base — Fused to the petiole.

*Petiole*.—Length — Average 22 mm. Diameter — Average 1 mm. Petiole color, adaxial and abaxial surfaces — Yellow-Green Group 146A. Margins — Stipitate glands present. Anthocyanin intonations — None. Prickles — Numerous prickles on the abaxial surface of the petiole. Stipitate glands — Abundant. Texture — Glabrous. Strength — Strong.

*Rachis*.—Length — Average 20 mm. Diameter — Average 1 mm. Color — Yellow-Green Group 146B. Anthocyanin intonations — Greyed-Purple Group 1876 present in immature foliage. Margins — Stipitate glands and very light pubescence. Prickles — A few small prickles underneath. Stipitate glands — Limited.

*Leaflets*.—Quantity — Normally 5 leaflets on normal leaves in middle of the stem. Dimensions — Average size of the terminal leaflet is 60 mm long and 35 mm wide. Shape — Ovate. Apex — Acute. Base — Obtuse. Margins — Serrated; no undulation. Luster and texture, adaxial surface — Semi-glossy and smooth. Luster and texture, abaxial surface — Matte and smooth. Juvenile foliage color, adaxial surface — Yellow-Green Group 146A. Juvenile foliage color, abaxial surface — Yellow-Green Group 146C. Mature foliage color, adaxial surface — Green Group 137A. Mature foliage color, abaxial surface — Yellow-Green Group 147B. Anthocyanin intonations — Greyed-Purple Group 183B. Intonations are predominantly present on abaxial surface of juvenile leaflets. Venation — Reticulate. Petiolule — Dimensions — 1 mm long and 1 mm in diameter. Petiolule color, adaxial surface — Green Group 137A with intonations of Greyed-Purple Group 183B. Petiolule color, abaxial surface — Yellow-Green Group 146B. Prickles — None present. Texture, adaxial and abaxial surfaces — Smooth. Margins — Stipitate glands.

Inflorescence:

*Inflorescence type*.—One to two pedicellate flowers are held upright on strong peduncles.

*Blooming habit*.—Recurrent; floriferous.

*Quantity of flowers*.—Generally one to two flower buds per peduncle.

*Size*.—10 cm tall and 6 cm wide, on average.

*Peduncle*.—Length — 20 to 23 mm average length. Diameter — 3 to 4 mm average diameter. Color — Yellow-Green Group 146A. Anthocyanin intonations — None. Strength — Strong. Texture — Smooth.

Flowering laterals: None present.

Bud:

*Bud form*.—Long; pointed ovoid.

*Size*.—Upon opening, 23 mm in length from base of receptacle to distal end of bud and 16 mm diameter at its widest point.

*Texture*.—Smooth.

*Color, as sepals first unfold*.—Yellow Group 4D.

*Color when one-quarter open, inner side*.—Marginal zone — Green-White Group 157C. Middle zone — Yellow-Green Group 150C. Basal zone — Yellow-Green Group N144C. General tonality — Green-White Group 157C.

*Color when one-quarter open, outer side*.—Marginal zone — Green-White Group 157A. Middle zone — Yellow-Green Group 150C. Basal zone — Yellow-Green Group N144C. General tonality — Green-White Group 157C.

Flower:

Pedicel:

*Surface*.—Fine hairs and stipitate glands are present.

*Length*.—45 to 50 mm, on average.

*Diameter*.—3 to 5 mm, on average.

*Color*.—Yellow-Green Group 144A.

*Anthocyanin intonations*.—Not present.

*Strength*.—Strong.

*Texture*.—Smooth.

Calyx:

*General*.—Comprised of five polysepalous sepals, with strong foliaceous appendages present on three of the five sepals.

*Diameter of calyx*.—60 to 65 mm, at anthesis.

*Sepals*.—Color, adaxial surface — Yellow-Green Group 146B. Color, abaxial surface — Yellow-Green Group 146A. Anthocyanin intonations — Not present. Size — 35 mm long and 9 mm wide, on average. Apex — Cirrose. Base — Flat at union with receptacle. Quantity — Five. Texture, adaxial surface — Smooth. Texture, abaxial surface — Rugose. Margins — Pubescent with stipitate glands. Stipitate glands — Limited number on the abaxial surface and along margins.

Corolla:

*General shape of corolla*.—Cup-open; deep.

*Shape of corolla when viewed from the side*.—Upon opening, upper portion — Flattened convex. Upon opening, lower portion — Flattened convex. Open flower, upper portion — Flattened convex. Open flower, lower portion — Flattened convex.

*Dimensions*.—Large for a miniature rose. When open, the average flower diameter is 70 to 75 mm and the average flower height is 50 to 60 mm.

*Fragrance*.—Very light.

*Duration*.—On the plant 14 to 17 days. Senesced petals clinging.

*Petals*.—Petal count — Exhibits double flowers with approximately 38 petals under normal conditions. Petal reflex — Slightly reflexed. Timing of petal reflex — Simultaneously. Petal margin — Entire. Petal shape — Obovate. Apex — Obtuse. Base — Obtuse. Dimensions — 33 mm long and 30 mm wide. Texture, inner surface — Smooth. Texture, outer surface — Smooth. Petal color, upon opening — Outermost petals, outer surface — White Group 155A. Outermost petals, inner surface — White Group 155A. Innermost petals, outer surface — White Group 155A. Innermost petals, inner surface — White Group 155B. Basal petal spots, upon opening — Basal petal spot, outermost petals — Dimensions — 9 mm high and 10 mm wide. Outer surface — Green-Yellow Group 1A. Inner surface — Green-Yellow Group 1A. Basal petal spot, innermost petals — Dimensions — 4 mm high and 10 mm wide. Outer surface — Green-Yellow Group 1A. Inner surface — Green-Yellow Group 1A. Petal color, after opening — Outermost petals, outer surface — White Group 155C. Outermost petals, inner — White Group 155C. Innermost petals, outer surface — White Group 155A. Innermost petals, inner surface — White Group 155B. Basal petal spots, after opening — Basal petal spot, outermost petals — No distinct coloration at the petal base. Basal petal spot, innermost petals — Dimensions — 4 mm high and 4 mm wide. Outer surface — No distinct coloration at the petal base. Inner surface — Green-Yellow Group 1B. General Tonality — White Group 155B. No change in general tonality at the end of the fourteenth day.

*Petaloids*.—Quantity — 2 petaloids per flower, on average. Dimensions — Highly variable; approximately 20 to 25 mm long and 5 to 15 mm wide. Color, outer surfaces — White Group 155A. Color, inner surfaces — White Group 155A to 155B. Margins — Highly irregular; entire to indented; non-undulating to undulated. Shape — Highly irregular; oval to spatulate to oblanceolate. Apex — Acute. Base — Attenuate. Texture, inner and outer surfaces — Smooth.

Reproductive organs:

*Stamens*.—Quantity — Approximately 160, on average, and regularly arranged around the styles. Anthers — Shape — Reniform. Dimensions — 2 mm long and 1 mm wide, on average. Color — Yellow-Orange Group 14A. Pollen — Medium density. Pollen Color — Greyed-Orange Group N163D. Filaments — Color — Yellow-Green Group 145A. Length — 5 mm.

*Pistils*.—Quantity — Abundant; approximately 80. Stigmas — Dimensions — 1 mm long and 1 mm wide. Location — Equal in position to anthers. Color — Yellow-White Group 158A. Styles — Length — Approximately 11 mm long. Color — Yellow-White Group 158A.

*Ovary*.—Dimensions — 3 to 40 mm long and 6 mm in diameter. Color — White Group 155B.

*Receptacle*.—Shape — Funnel-shaped. Dimensions — Approximately 7 mm high and 8 mm wide. Surface — Glabrous and smooth. Color — Yellow-Green Group 146B.

Hips and seed formation: Not observed.

COMPARISONS WITH THE PARENT

The new rose plant may be distinguished from its parent, 'KORpot042', by the coloration of the flower. 'KORpot068' exhibits a cream white flower color, whereas 'KORpot042' exhibits a salmon flower color.

COMPARISON WITH THE MOST SIMILAR *ROSA* CULTIVAR KNOWN TO THE INVENTOR

For a comparison, several physical characteristics of the rose variety 'KORpedia', a rose variety from the same inventor described and illustrated in U.S. Plant Pat. No. 19,638 are compared to 'KORpot068' in Chart 1.

CHART 1

| Characteristic | 'KORpot068' | 'KORpedia' |
|---|---|---|
| General tonality of the flower. | White Group 155B. | Yellow Group 2D. |
| Average size of terminal leaflet, | 60 long and 35 mm wide. | 45 mm long and 25 mm wide. |
| Flower petal count. | 38. | 30 to 35. |

That which is claimed:

1. A new and distinct variety of rose plant named 'KORpot068', as described and illustrated herein.

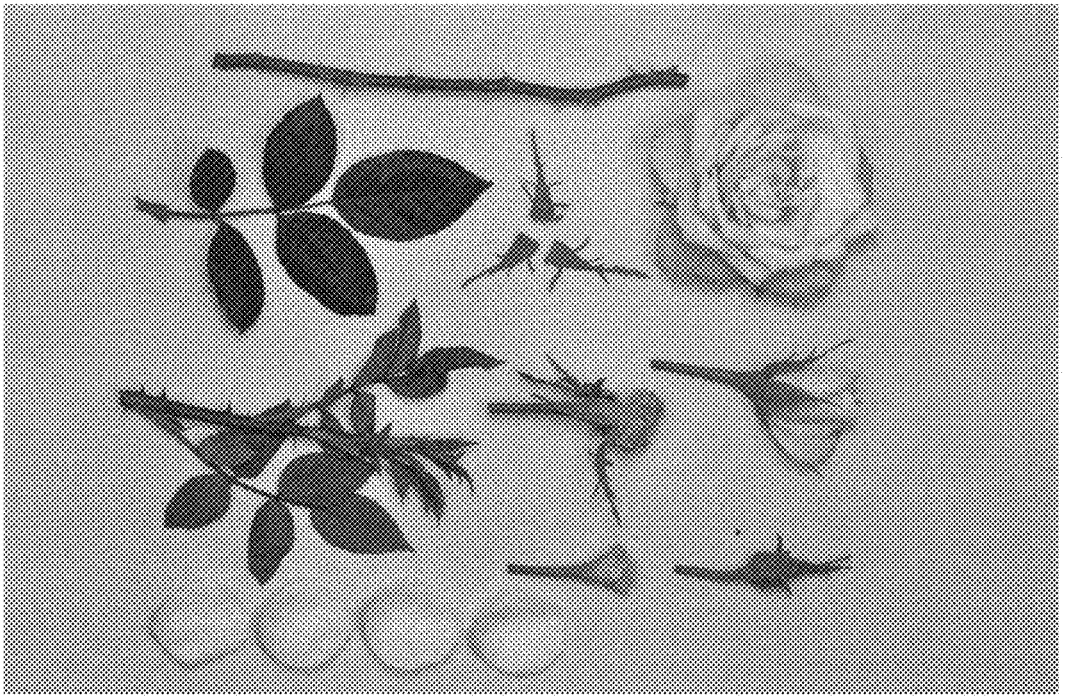

* * * * *